United States Patent [19]

Hildreth et al.

[11] 4,256,671

[45] Mar. 17, 1981

[54] PRODUCTION OF 2,4- AND 2,6-DIAMINOTOLUENES

[75] Inventors: John D. Hildreth, Macclesfield; David G. Haslam, Bolton; David E. Allen, Wilmslow, all of England

[73] Assignee: Clayton Aniline Company, Ltd., Clayton, England

[21] Appl. No.: 38,296

[22] Filed: May 11, 1979

Related U.S. Application Data

[63] Continuation-in-part of Ser. No. 923,721, Jul. 11, 1978, abandoned.

[30] Foreign Application Priority Data

Nov. 24, 1977 [GB] United Kingdom ............... 48948/77

[51] Int. Cl.³ ....................... C07C 85/11; C07C 85/26
[52] U.S. Cl. .................................... 564/422; 260/689; 564/423; 564/437
[58] Field of Search ..................... 260/580, 689, 582

[56] References Cited

U.S. PATENT DOCUMENTS

| | | | |
|---|---|---|---|
| 2,884,457 | 4/1959 | Ferstandig | 260/582 X |
| 2,976,320 | 3/1961 | Winstrom et al. | 260/580 |
| 3,136,818 | 6/1964 | Sperber et al. | 260/689 X |
| 3,847,989 | 11/1974 | Platz et al. | 260/689 X |

FOREIGN PATENT DOCUMENTS

16936 of 1914 United Kingdom .................... 260/580

*Primary Examiner*—John Doll
*Attorney, Agent, or Firm*—Wenderoth, Lind & Ponack

[57] ABSTRACT

A process for the manufacture of 2,4- and 2,6-diaminotoluenes comprises catalytically hydrogenating the corresponding molten nitro compound in the presence of water, adding hydrochloric acid to form the monohydrochlorides, crystallizing 2,6-diaminotoluene monohydrochloride, filtering it off and, if desired, liberating the free bases by addition of an alkali.

7 Claims, No Drawings

PRODUCTION OF 2,4- AND 2,6-DIAMINOTOLUENES

The present application is a continuation-in-part of application Ser. No. 923,721, filed July 11, 1978.

The present invention relates to the production of aromatic amines.

Aromatic amines are important starting materials for the manufacture of dyestuffs and pigments by diazotisation followed by coupling with various coupling components. It is known that aromatic amines can be prepared by catalytic hydrogenation of the corresponding nitro compound, the reactions having been performed in solution in various solvents or in the vapour phase.

We have now surprisingly found that molten aromatic nitro compounds can be reduced in the melt, giving much greater productivity and avoiding the problem of recovering the product from the solvent, which involves expensive distillation, or in handling compounds in the vapour phase. The product can be easily separated from the resulting aqueous layer and the catalyst filtered off, or in some cases, after removal of catalyst, the whole of the product mixture including the water can be used intact, e.g. to be diazotized prior to coupling.

Accordingly, the present invention provides a process for the manufacture of aromatic amines which comprises catalytically hydrogenating the corresponding molten nitro compound, the nitro compound having a melting point of above 5° C.

Suitable nitro compounds include those of the general formula:

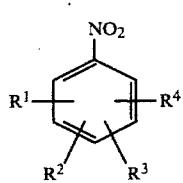

in which $R^1$, $R^2$, $R^3$ and $R^4$ are the same or different and represent hydrogen, halogen, nitro, hydroxy, cyano, carboxyl and substituted or unsubstituted alkyl, alkoxy, aryl, aralkyl, aryloxy, or arylsulphone groups, or mixtures of such compounds.

Preferably the nitro compound is one which is solid at ambient temperatures.

The catalyst may be any that is known for carrying out catalytic hydrogenation reactions, such as nickel, platinum, palladium ruthenium and rhodium. We prefer to use palladium on charcoal as the catalyst, in suitable catalytic amounts. The amount of catalyst may be varied over a wide range and may be from 0.005% to 0.1%, based on the weight of the nitro compound. We prefer to use about 0.01%.

The reaction is carried out at a temperature above the melting point of the nitro compound being reduced and above the melting point of the resulting amine. Once the nitro compound has been melted it is not necessary to heat to a higher temperature, although this may be done if desired, for example in the case of nitro compounds having a low melting point, to increase the speed of the reaction.

The reaction may be carried out under elevated pressure which may be from 15 to 1400 psi, preferably from 70 to 420 psi. The temperature of the reaction may be up to 150° C., preferably up to 120° C., providing that both the starting material and product are both liquid at the temperature used.

The reaction is continued until consumption of hydrogen ceases, which may take from 1½ to 10 hours. The time taken is dependent on the temperature and pressure used in the reaction, the catalyst concentration and on the efficiency of the mixing during the reaction. For example, reaction times may be reduced by carrying out the hydrogenation in a spray nozzle high circulation reactor, such as a Buss loop reactor. Such a loop reactor normally renders an enhanced selectivity to the catalyst through more efficient mixing and cooling of the exothermic reaction. After uptake of hydrogen ceases, it is preferred to maintain the reaction conditions for an additional time, e.g. up to 30 minutes, preferably about 15 minutes to ensure that the reaction is complete.

Before the hydrogenation is started, the reactor should be purged to remove oxygen. The purging can be carried out using an inert gas, such as nitrogen or, preferably, hydrogen.

The process of the invention can be applied to various aromatic nitro compounds. These include, for example, p-nitrotoluene, 2-nitrobenzenesulphon-N-ethylanilide and 2-nitrobenzenesulphon-N-cyclohexylamide, 2,4-dinitrotoluene, 2,6-dinitrotoluene and mixtures of 2,4- and 2,6-dinitrotoluene.

The present invention is particularly suited to the hydrogenation of a mixture of 2,4- and 2,6-dinitrotoluene as, when the hydrogenation is carried out in the presence of water, the resulting diamines are obtained in a sufficiently pure form to enable their easy separation and further use in the production of dyestuffs without further purification.

Accordingly the invention provides a process for the manufacture of 2,4-diaminotoluene and 2,6-diaminotoluene from a mixture of 2,4- and 2,6-dinitrotoluene which comprises catalytically hydrogenating a molten mixture of 2,4- and 2,6-dinitrotoluene in the presence of water, adding sufficient hydrochloric acid to form the diaminotoluene monohydrochlorides, crystallising 2,6-diaminotoluene monohydrochloride and filtering it from the 2,4-diaminotoluene monohydrochloride and then liberating the free amine, if desired, by addition of an alkali, such as caustic soda.

Some water is formed during the hydrogenation, but additional water is needed for the separation. At least some of this additional water is added before hydrogenation begins and the water formed during the hydrogenation is retained in the reaction vessel. The presence of additional water at the beginning of the reaction helps to ensure that the reaction is carried out safely.

The 2,6-diaminotoluene monohydrochloride obtained as a filter cake can be converted into the free base by rendering it alkaline. The resulting free base contains only very small amounts of the 2,4-diaminotoluene, usually less than 0.5%, and is of excellent quality, retaining its original very pale grey colour over long periods of time.

The molten liquor remaining after filtration contains the 2,4-diaminotoluene monohydrochloride in a sufficiently pure state to be usable directly for the preparation of dyestuffs by diazotisation followed by coupling.

The invention is illustrated by the following Examples, in which parts by weight bear the same relationship to parts by volume as do kilograms to liters.

EXAMPLE 1

To a shaking autoclave was charged 451 parts by weight of molten p-nitrotoluene and a mixture of 2.25 parts by weight of catalyst comprising 5% palladium on charcoal as a 50% paste, and 10 parts by volume water (to mix the catalyst). The reactor was closed and purged with hydrogen and the p-nitrotoluene was then hydrogenated at a pressure of 70 p.s.i. and at a temperature of 100°–105° C. These conditions were maintained for 4 hours when consumption of hydrogen ceased, and then a further 15 minutes to ensure that the reduction was complete. The product was cooled to 95° C., the pressure was released and the catalyst filtered off. The autoclave and catalyst were washed with 50 parts by volume of water at 90° C. The reaction mass was collected in a separation vessel, allowed to cool to 55° C. and then settled for 5 minutes. The product formed a lower organic layer which was run off. The product, p-toluidine was obtained in a yield of 97.7% theory.

EXAMPLE 2

To a shaking autoclave was charged 420 parts by weight of 2-nitrobenzenesulphon-N-ethylanilide as a melt at 95°–98° C. and a mixture of 4.2 parts by weight catalyst comprising 5% palladium on charcoal as a 50% paste, 8.4 parts by weight sodium bicarbonate and 15 parts by volume water (to mix the catalyst). Hydrogenation was carried out at a pressure of 210 p.s.i. and a temperature of 115°–120° C. for 4 hours after which consumption of hydrogen ceased. The reaction conditions were maintained for a further 15 minutes to ensure that the reduction was complete.

The pressure was released and the reaction mass run into a separate vessel and cooled to 75° C. 106 Parts by volume of isopropyl alcohol (as 87% isopropyl alcohol, 13% water by weight) and the mixture heated with agitation to 80° C. The catalyst was filtered off at 80° C. The catalyst and autoclave were washed with 106 parts by volume isopropyl alcohol (87% by weight) and this was retained for the next operation.

The filtered reaction mass was run into 1800 parts by volume water at 60° C. containing 7.6 parts by weight of a dispersing/wetting agent. The mixture was cooled with rapid agitation to 25° C. to crystallize the mass. The product, 2-aminobenzenesulphon-N-ethylanilide was filtered and washed with cold water, the yield being 95.0% of theory.

EXAMPLE 3

To a shaking autoclave was charged 284 parts by weight of 2-nitrobenzenesulphon-N-cyclohexylamide as a melt at 85°–90° C. and a mixture of 1.4 parts by weight catalyst, comprising 10% palladium on charcoal as a 50% paste, 1.5 parts by weight sodium bicarbonate and 5 parts by volume water (to mix the catalyst). Hydrogenation was carried out at a pressure of 210 psi. and a temperature of 115°–120° C. for 4 hours after which consumption of hydrogen ceased. The reaction conditions were maintained for a further 15 minutes to ensure that the reduction was complete.

The pressure was released and the reaction mass run into a separate vessel and cooled to 75° C. 62 Parts by volume of isopropyl alcohol (as 87% isopropyl alcohol, 13% water by weight) were added and the mixture heated to 80° C. with agitation. The catalyst was filtered off at 80° C. The autoclave and catalyst were washed with 62 parts by volume of 87% by weight isopropyl alcohol which was retained for the next operation.

The filtered reaction mass was run into 1220 parts by volume water at 60° C. containing 5 parts by weight of a dispersing/wetting agent, with good agitation. The mixture was cooled to 25° C. to crystallise. The product, 2-aminobenzenesulphon-N-cyclohexylamide, was filtered and washed with cold water, the yield being 97.0% of theory.

EXAMPLE 4

To a shaking autoclave was charged 210 parts by volume warm water (approximately 50° C.) and 136 parts by weight of a 2,4/2,6-dinitrotoluene mixture (approx. 50:50) previously melted at about 30°–35° C. The pH was adjusted to 7.0–7.5 and 2.72 parts by weight of catalyst comprising 5% palladium on charcoal as a 50% paste, were added. The reactor was closed and purged with hydrogen. The nitro compounds were then hydrogenated at a pressure of 70 p.s.i. and a temperature of 100° C. for 3¼ hours, after which consumption of hydrogen ceased. The reaction conditions were maintained for a further 15 minutes to ensure that the reduction was complete.

The reaction mass was cooled to 90° C., the pressure was released and the catalyst filtered off. The reactor and catalyst were washed with 81 parts by volume hot water and the final volume was adjusted to 406 parts.

3 Parts by volume sodium bisulphite solution (40% w/w–25% $SO_2$) and 0.5 parts by weight ascorbic acid were added as antioxidants, and the temperature adjusted to 72° C. The solution was then estimated for total amine content, so that the exact amount of hydrochloric acid required for the separation of 2,6-diaminotoluene as monohydrochloride could be calculated. With good agitation, 97 parts by weight hydrochloric acid, S.G. 1.14 were added, during which the temperature rose to 80° C. and the pH fell to 2.5 to 3.5. At 80° C. and with slow agitation, 98 parts of sodium chloride were added over 1½ hours. The mixture was then cooled to 40° C. and filtered. The liquors contain 2,4-diaminotoluene hydrochloride.

The filter cake was washed with water containing sodium chloride and ascorbic acid, the product being 2,6-diaminotoluene hydrochloride.

EXAMPLE 5

The 2,6-diaminotoluene monohydrochloride filter cake obtained in Example 4 was converted into the 2,6-diaminotoluene free base by charging the whole of the filter cake, with good agitation, into 38 parts by volume water at 85° C. and containing 1.0 part by volume sodium hydroxide solution S.G. 1.35 and 0.2 parts of ascorbic acid.

Approximately 32 parts by weight sodium hydroxide solution S.G. 1.35 were then added carefully over 15 minutes so that the pH at the end of the addition was 8.0–8.5. The mixture was stirred for 1 hour at 85° C. while checking and maintaining pH 8.0–8.5 and then cooled to 20° C. to allow the oil to crystallize followed by neutralization to pH 7.0 with a little hydrochloric acid.

The crystalline 2,6-diaminotoluene was filtered at 20° C. and the filter cake washed with 40 parts by volume water containing 0.1 parts ascorbic acid. The product was dried under vacuo to yield 33.2 parts 2,6-diaminotoluene free base 100% mol. wt. 122 of excellent quality (≦0.5% 2,4-diaminotoluene content) and aspect. The material was resistant to discolouration by air oxidation and retained its original very pale grey colour over long periods of time.

EXAMPLE 6

The mother liquors remaining after separation of the 2,6-diaminotoluene as monohydrochloride in Example 4 were converted to dyestuff as follows:

Approximately 450 parts by volume mother liquors at approximately 10.7% w/v diaminotoluene content ≡48.1 parts 100% mol. wt. 122 (approximately 93–95% 2,4-diaminotoluene and 5–7% 2,6-diaminotoluene) were treated with 24.8 parts by volume sodium hydroxide solution S.G. 1.50 to raise the pH to 8.5. The mixture was cooled to 0°–2° C. and the volume adjusted to 1620 parts with ice and water. 52.2 Parts by volume sodium nitrite solution 5 N were added and stirred for 5 minutes to mix.

103.5 Parts by volume hydrochloric acid S.G. 1.14 were added over 1½ minutes and the mixture stirred for 2 minutes at 10°–12° C.

45 Parts by volume sodium hydroxide solution S.G. 1.50 were then run in over 1½ minutes and the mixture stirred for 15 minutes (alkaline to phenolphthalein).

The dyestuff was precipitated by addition of 12.2 parts by volume hydrochloric acid S.G. 1.14 and 66 parts sodium chloride followed by stirring overnight. After filtration and drying the dyestuff was obtained in a yield of 15 parts and particularly suitable for the dyeing of paper.

Alternatively, a liquid dyestuff preparation can be prepared as follows:

After making the mixture alkaline to phenolphthalein as above, heat to 50° C. and maintain 1 hour at this temperature. Filter and wash the filter cake with 1450 parts water. Charge the filter cake into 40 parts by volume acetic acid 60% w/w and stir for 2 hours at pH 4.2–4.5 to dissolve.

We claim:

1. A process for the manufacture of 2,4-diaminotoluene and 2,6-diaminotoluene from a mixture of 2,4- and 2,6-dinitrotoluene which comprises catalytically hydrogenating a molten mixture of 2,4- and 2,6-dinitrotoluene in the presence of water, adding sufficient hydrochloric acid to form the diaminotoluene monohydrochlorides, crystalising 2,6-diaminotoluene monohydrochloride and filtering it from the 2,4-diaminotoluene monohydrochloride and optionally, liberating the free amine by addition of an alkali.

2. The process of claim 1, wherein the catalyst is nickel, platinum, palladium, ruthenium or rhodium.

3. The process of claim 2, wherein the catalyst is palladium on charcoal.

4. The process of claim 1, wherein the amount of catalyst is 0.005% to 0.1% based on the weight of the dinitrotoluenes compound.

5. The process of claim 1, wherein the reaction is carried out at a pressure of from 15 to 1400 p.s.i.

6. The process of claim 1, which is carried out in a loop reactor.

7. The process of claim 1, wherein the free amine is liberated by use of caustic soda.

* * * * *